United States Patent [19]

Hansen

[11] Patent Number: 4,621,068
[45] Date of Patent: Nov. 4, 1986

[54] PROCESS FOR PREPARING POLYMER PARTICLES

[75] Inventor: Ove E. Hansen, Lille Varløse, Denmark

[73] Assignee: A/S Niro Atomizer, Soborg, Denmark

[21] Appl. No.: 734,670

[22] Filed: May 16, 1985

[30] Foreign Application Priority Data

May 22, 1984 [DK] Denmark .............................. 2519/84

[51] Int. Cl.$^4$ .............................................. B01J 35/08
[52] U.S. Cl. ......................................... 502/8; 423/338
[58] Field of Search .............. 502/8; 252/315.1, 315.5, 252/315.6; 423/338

[56] References Cited

U.S. PATENT DOCUMENTS

| | | | |
|---|---|---|---|
| 2,921,839 | 1/1960 | Ritter | 423/339 |
| 4,011,096 | 3/1977 | Sandell | 502/8 X |
| 4,089,932 | 5/1978 | Morita et al. | 423/338 |

Primary Examiner—W. J. Shine
Attorney, Agent, or Firm—Dennison, Meserole, Pollack & Scheiner

[57] ABSTRACT

Substantially spherical solid particles of a substantially uniform particle size are prepared by dispersing a solution of a polymerizable substance in a first liquid by means of a suitble emulsifier to form droplets of the polymerizable substance of a substantially uniform particle size, which are thereafter poured into a second liquid with which the first liquid is immiscible and which contains a sufficient amount of a reactant to polymerize the polymerizable substance. After the polymerization the substantially spherical particles formed are recovered. In a preferred embodiment, an aqueous solution of an alkaline metal silicate, especially sodium silicate, is dispersed in a coparaffinate by means of a suitable emulsifier, and the emulsion is poured into an aqueous solution of the polymerization reactant to form gelled, substantially spherical hydrated silicate particles.

35 Claims, 4 Drawing Figures

PROCESS FOR PREPARING POLYMER PARTICLES

BACKGROUND OF THE INVENTION

1. Field of the Invention

The present invention relates to a process for preparing substantially spherical polymer particles, in particular polymer particles of substantially uniform particle size.

2. Description of Prior Art

Polymer particles of a substantially uniform particle size, in particular particles of an inorganic polymer such as amorphous silica, are used for various applications, e.g., as carriers for chromatography, such as high performance liquid chromatography. Chromatographic separation methods have become increasingly important in recent years, not only for the purpose of chemical analysis, but also in industrial (preparative) separation processes, e.g., in the pharmaceutical industry as outlined in, e.g., *Process Engineering*, February 1984, pp. 26-31.

The polymer particle material used for such chromatographic separations should meet various requirements which are mentioned, e.g., in *J. Chromatography* 83, 1973, pp. 5-9. For instance the material should be composed of small spherical particles of a uniform particle size. With a narrow particle size distribution, a smaller flow resistance in the chromatographic column is obtained, and the smaller the particle size, the greater the separation efficiency. However, a lower limit of about 5 μm in particle size is determined by the difficulty in packing the chromatography columns with any degree of reproducibility.

Another important parameter is the pore structure which depends on the type of chromatography to be employed. The desired pore diameter also depends on the substances to be separated. In the above-mentioned article from *J. Chromatography* a distinction is made between macropores which should be ten times smaller than the particle diameter, and micropores which should be about two and a half times the diameter of the molecule of the substance which is to be absorbed in the chromatography separation process. The pore volume should be as large as possible; however, with increasing pore volume, the stability with regard to the pressure used in packing the column (up to 500 bars) decreases and it has been found that the pore volume should not exceed about 1.7 cm$^3$/g.

In the methods of preparing such particles known to the present inventor, a large particle size distribution is obtained so that it is necessary to fractionate the resulting product which consequently increases the production costs.

SUMMARY OF THE INVENTION

The present invention provides a simple and inexpensive way of producing polymer particles having the desired characteristics and having a narrow particle size distribution which ensures that the particles prepared may be used directly without any fractioning.

Accordingly, the present invention provides a process for preparing substantially spherical solid particles of a substantially uniform particle size, said method comprising dispersing a solution of a polymerizable substance in a first liquid by means of a suitable emulsifier to form droplets of the polymerizable substance of a substantially uniform particle size, pouring the emulsion into a second liquid with which the first liquid is immiscible and which contains a sufficient amount of a reactant to polymerize the polymerizable substance, and recovering the polymerized, substantially spherical particles of the polymerizable substance thus formed.

Such particles are known, e.g. from U.S. Pat. No. 2,921,839. This patent, however, describes a different production method, namely by polymerizing the substance by adding the polymerization reactant to the emulsion under vigorous agitation so that the polymerization takes place in the emulsion. U.S. Pat. No. 4,089,932 describes a process for the preparation of spherical silica gel in which water glass is emulsified when dispersed in a solvent to form a silica gel sol which is gelled in emulsified state. EP 58441 describes the preparation of a sol within a capillary tube, which is vibrated. The sol is formed when the drops leave the tube. However, the size of the drops is of the same order of magnitude as the diameter of the tube, i.e. much larger than the size of drops to be used in the formation of an emulsion.

In accordance with the principles of the present invention it has surprisingly been found more advantageous to prepare an emulsion in order to obtain a uniform size distribution and thereafter add the emulsion to the second liquid containing the polymerization reactant instead as this ensures that the polymerizable substance is more readily accessible to the polymerization reactant and that, consequently, a more uniform polymerization takes place, resulting in a more even shape of the polymerized particles.

In the present context the term "polymerizable substance" designates any substance which is able to form a polymer or a polymer-like structure, either by itself or by chemical combination with another substance. The term "polymer or polymer-like structure" designates any structure built up from a multiplicity of individual subunits which may or may not be identical such as monomeric or oligomeric molecules or ions. As examples of polymerizable substances which may be prepared into particles by the method of the invention may be mentioned monomeric or oligomeric units composing inorganic or organic, natural or synthetic polymers such as silicones or siloxanes, polyamides, acrylics, polyesters, polyvinyl halides, polyethylene, polystyrene, polypropylene, polyurethane, polysaccharides, and polypeptides. In the present context, the term "polymerizable substance" also includes inorganic gel-forming compounds, primarily alkali metal silicates, aluminates or zirconates, in which the alkali metal may be lithium, sodium or potassium. A favoured alkali metal silicate is sodium silicate. The organic gel-forming substance may also be a silica sol (colloidal solution) such as the one disclosed in U.S. Pat. No. 2,757,073.

In the present context, the term "first liquid" is understood to mean any liquid which is substantially immiscible with the solution of the polymerizable substance emulsified therein. It is also understood that the first liquid includes a suitable emulsifier.

Apart from being substantially immiscible with the second liquid, the first liquid preferably has a density which differs significantly from that of the second liquid in order to facilitate a separation of the phases; preferably, the first liquid has a lower density than than the second liquid. Thus, the first liquid may be an organic liquid such as 1. aliphatic straight-chain, branched chain or cyclic, saturated or unsaturated, optionally halogenated hydrocarbons, in particular $C_{5-10}$ hydrocarbons, in particular hexanes, heptanes, octanes, nonanes, dichloromethane etc.,
2. aromatic hydrocarbons which are optionally substituted with aliphatic side chains, such as benzene, toluene, and xylene,
3. higher alcohols such as $C_{8-11}$, saturated or unsaturated aliphatic alcohols, in particular fatty alcohols,
4. coparaffinates,
5. fatty esters such as triglycerides, e.g. vegetable or animal oils.

It is preferred that the organic liquid combines the qualities of not being a health hazard and of being inexpensive; an example of one such substance is a coparaffinate such as ISOPAR, available from Esso (cf. the Merck Index, 10th Edition, item 2490) (ISOPAR is a registered trademark).

The nature of the second liquid is less essential, provided that it is substantially immiscible with the first liquid and contains a polymerization reactant for the polymerizable substance. The second liquid should also preferably be suitable for being readily separated from the first liquid, e.g. by phase separation and decantation. The term "polymerization reactant" is intended to include both substances which, in the polymerization reaction, combine with the polymerizable substance to form the final polymer and catalysts which initiate polymerization, but do not form part of the final product.

The second liquid may be a liquid which is identical to the solvent for the polymerizable substance, or it may simply be miscible with this solvent. If the polymerizable substance is an organic monomer, the second liquid may suitably be a organic solvent for the monomer, such as one of those mentioned above (in which case the first liquid may be water or an aqueous solution and the emulsion may be an oil-in-water type emulsion), and the polymerization reactant is selected among those which are known to initiate polymerization of the monomer in question. When the polymerizable substance is an inorganic gel-forming substance, such as one of those defined above, the second liquid may advantageously be water or an aqueous solution and the emulsion may be a water-in-oil type emulsion, and the polymerization reactant may be an acid or acid buffer. In some cases, such as when the polymerizable substance is a silica sol, the polymerization reactant may also be a weak base such as an ammonia solution.

When dealing with water-soluble substances, such as gel-forming alkali metal salts, it is surprising that water may be used as the second liquid, as it would be expected that the droplets of the polymerizable substance in the emulsion, when added to the water containing the polymerization reactant, would disintegrate and form a continuous gel. It is assumed that the droplets retain their shape because the first liquid which is substantially immiscible with water, together with the emulsifier forms a thin film around each droplet of the polymerizable substance which allows the polymerization reactant (such as H+ ions) to pass through to initiate gelling faster than it allows the aqueous solution of the polymerizable substance to permeate through it into the water.

Depending on the intended use of the particles, it is possible to produce particles of any size in the size range of 1–100 μm which shows a narrow size distribution. The particle size distribution is suitably expressed by referring to a figure Dx in which D is the diameter in μm which x percent by volume of the particles are equal to or smaller than in size. Thus, for instance, D50 is an expression of the mean particle diameter defined as the diameter which 50% by volume of the particles are equal to or smaller than in size; correspondingly, D10 and D90 designate the diameter which 10% and 90% by volume, respectively, of the particles are equal to or smaller than in size. The term "slope" is used to indicate the narrowness of the particle size distribution expressed as D90 divided by D10; roughly, the figure for slope expresses how many times the size of the larger particles exceeds that of the smaller particles. If D90=D10, slope equals 1 which means that the particles are all of the same size; therefore, the more closely the figure for slope approximates 1, the more uniform is the particle size. To obtain particles with the desired characteristics, slope should not exceed 7, preferably not 4, in particular not 3.

The particle diameter (as a measure for particle size) may be determined e.g. by passing a monochromatic laserbeam through an optical cuvette containing a dispersion of the particles. The particle diameter may then be calculated from the angle at which the light is scattered. A suitable apparatus for this purpose is, e.g., a Microtrack apparatus (manufactured by Leeds and Northrop).

In a preferred embodiment of the process of the invention, an aqueous solution of an alkali metal silicate, especially sodium silicate, is dispersed in a coparaffinate by means of a suitable eulsifier, and the emulsion is poured into an aqueous solution of the polymerization reactant to form gelled, substantially spherical hydrated silica particles. The concentration of sodium silicate in the aqueous solution is about 8–20%, and the sodium silicate employed preferably has the formula $Na_2O(SiO_2)_x$, wherein x is in the range of 3–4. According to the invention, it has been found that the silicate concentration is a decisive parameter for pore volume and pore diameter in the resulting silica particles in that a higher silicate concentration tends to result in a smaller pore volume and pore diameter. The concentration of sodium silicate in the starting material employed should therefore be selected in accordance with the desired pore volume and pore diameter of the final product.

In this system, the emulsifier is suitably an emulsifier with an HLB value of less than 6, preferably an HLB value between 2 and 5 such as an HLB value of about 3–4. Emulsifiers useful for this purpose are selected from monoesters of $C_{14-20}$ fatty acids, especially monoesters of $C_{16-18}$ fatty acids, such as stearic, oleic, palmitic, myristic, linoleic, or linolenic acid with a polyhydric alcohol such as sorbitol or glycerol. Specific esters of this type are, e.g., sorbitol monooleate, glycerol monolaurate, glycerol monooleate, and glycerol monostearate.

In this preferred embodiment, the aqueous solution of sodium silicate emulsified in coparaffinate is polymerized by being poured into a second liquid which is an aqueous buffer. The buffer is preferably of a pH in the range of 4–7 and is preferably present in a volume which is sufficient to maintain a final pH in the mixture of the emulsion and the aqueous buffer of below about 7. The buffer may be any suitable acid buffer such as a phosphate or citrate buffer, but is preferably an acetate buffer, and the acetate buffer is present in a volume sufficient to maintain a pH in the mixture of about 5.3.

After the polymerization, the polymerized, substantially spherical hydrated silica particles may be subjected to ageing by heat treatment and/or acid treatment in an aqueous medium to adjust the pore diameter and pore volume of the particles, e.g., a treatment in an aqueous medium of a pH of less than 8, such as, e.g., dilute hydrochloric or sulphuric acid, preferably at a temperature above about 80° C. This ageing is another important parameter for adjusting the pore diameter and pore volume of the particles. It is known (e.g. from Iler, Ralph K. "The Chemistry of Silica. Solubility, Polymerization, Colloid and Surface Properties, and Biochemistry", a Wiley-Interscience Publication, John Wiley & Sons, New York-Chichester-Brisbane-Toronto, 1979) that silica gel particles polymerize further when subjected to heat treatment so that they shrink less on drying. Consequently, the pore volume and pore diameter does not decrease as much as in unaged silica particles. A convenient way to perform the heat treatment is simply to boil the newly formed particles in the second liquid before they are separated off and dried. It has been found possible to adjust the pore volume and pore diameter almost at will (though dependent on the silicate concentration as mentioned above) by specifying the time and temperature at which the heat treatment is carried out.

The separation of the particles from the second liquid may suitably be performed by decantation and filtration, suitably after the first liquid has been removed by phase separation and decantation. The particles are suitably washed with deionized water. A further narrowing of the particle size distribution may be obtained by decantation 1–2 times after standing for about 12 hours.

The drying of the particles may be performed by heating, e.g., in an oven, e.g. at a temperature of above 100° C., such as a temperature in the range of 100°–150° C., typically 120°–140° C.

An increase of the compressive strength of the silica particles may be obtained by calcination, e.g. at 300°–600° C., such as 400°–500° C., typically about 450° C., for e.g. about 2–5 hours such as about 3 hours. In this way, the counterpressure in the chromatography column will be reduced as fewer particles will collapse under the high pressure used in packing the column. Although the calcination could, in principle, be performed at higher temperatures such as temperatures of the order of about 900° C. with increasing beneficial effect with respect to reducing the counterpressure, this is normally not preferred, as it might tend to impede the chromatographic properties of the particles.

The polymerized, substantially spherical particles prepared by the process described above are primarily intended for use as carriers for various types of liquid chromatography, such as partition (reverse phase), adsorption, ion exchange or gel permeation chromatography, especially high performance liquid chromatography, or other types of chromatography such as affinity chromatography. However, such particles—depending on their composition—are useful for any purpose requiring substantially spherical particles of a uniform particle size, such as carriers for catalysts, carriers for the immobilisation of enzymes or for peptide synthesis, etc.

The dispersion of the solution of the polymerizable substance in the first liquid may, for example, be performed by suitable agitation, such as by vigorous stirring or by vibration. The effect supplied to the mixture by the stirring, or by the parameters of the vibration, including the frequency and amplitude, influences the particle size. Thus, it has been found that ultrasonic vibration will tend to result in a very small particle size which is hardly useful for chromatography, but which may, of course, be interesting for other purposes, e.g., where the particles are to be used as ultrafine fillers in matrixbound materials with an organic or inorganic binder matrix. On the other hand, vibration at a frequency in the range of 30–1000 Hz, in particular 40–150 Hz, will result in particle sizes useful for chromatographic purposes. The vibration may typically be performed at an amplitude in the order of millimeters or centimeters. Generally speaking, the desired particle size may be expressed according to the formula: particle diameter$^n$ = constant × frequency$^2$ × amplitude; the higher the frequency and amplitude, the smaller the particle diameter. The mixture may be subjected to the stirring or vibration batchwise, or the stirring or vibration may be performed in a continuous process.

The polymerizable substance may be dispersed in the first liquid by simultaneously and continuously feeding the solution of the polymerizable substance and the first liquid, which contains a suitable emulsifier, into a substantially cylindrical, elongated passage defined in a body member at such a flow rate that the passage is not filled up by the liquids to be emulsified, and by vibrating the body member.

The vibration is preferably performed at a frequency in the range of 30–1000 Hz, especially 40–150 Hz, and the body member is preferably vibrated at an amplitude ranging from about 1 mm to about 3 cm to obtain particles of a size in the range of 1–100 μm.

In practice, it has been found suitable that the passage is arranged at an acute angle to the horizontal plane, such as an angle of 10°–30°.

For the preparation of particles in a size range useful for chromatography, the passage should have an inner cross-section the transverse minimum width of which is 10–30, especially 15–25, in particular 18–20 mm and a length between 0.5 and 3 m, especially between 1 and 3 m.

The body member may suitably be vibrated by means of, e.g., a ball vibrator (a vibrator which produces vibrations by means of a ball made to rotate in a circular track defined in a housing) operated by means of compressed air.

The body member subjected to the vibration is suitably suspended by means of resilient suspension means such as springs or suspensions of an elastic material.

The body member is suitably a substantially circularly cylindrical tube having in inner diameter of 10–30, especially 15–25, in particular 18–20, mm and a length between 0.5 and 3.0 m, especially between 1 and 3 m.

However, the presently preferred method of carrying out the emulsifying step of the process comprises pressing the polymerizable substance and the first liquid together with the emulsifier through one or more nozzles. This method is particularly suitable for large scale production.

The method is similar to the homogenization technique used in the dairy industry. A description of that technology is given in Mulder H. & P. Walstra, *The milk fat globule*, Emulsion science as applied to milk products and comparable foods, Commonwealth Agricultural Bureaux, Farnham Royal, Bucks., England, and Centre for Agricultural Publishing and Documentation, the Netherlands (1974).

It should be noted, however, that the purpose of homogenizing milk products is to break down the fat globules into smaller globules in order to effectively prevent sedimentation of fat.

In the process of the present invention the aim is to obtain droplets of the polymerizable substance of a substantially uniform particle size.

Homogenization of milk reduces the mean diameter of the fat globules from 3–4 μm by a factor of about 10 and yields a broad particle size distribution, whereas the desired mean diameter in the process of the invention is typically 5–30 μm.

In this preferred embodiment of the process according to the invention the polymerizable substance is emulsified in the first liquid by simultaneously and continuously forcing a solution of the polymerizable substance and the first liquid, which contains a suitable emulsifier, through an orifice or a plurality of orifices placed in series.

In its simplest form the orifice is a circular hole with a diameter of 0.5–5 mm.

If the requirements to a narrow particle size distribution are not critical one orifice may be sufficient. Usually, however, several orifices are used. Since the emulsifying effect of any additional orifice decreases with the total number of orifices, more than 20 are seldom used. A number of 5–10 is optimal for most purposes. When several orifices are used the diameter of each one is normally but not necessarily the same.

The particle diameter obtained depends on a number of variables. From the above cited literature reference it is possible to derive at the following relationship.

$$D50 \times f^n = K \times d^{2n}$$

in which
D50 = the mean particle diameter
F = total flow rate
n = a product variable
K = a constant for a given system and product
d = orifice diameter The values of n and K can be determined experimentally.

In known processes for milk homogenization the value of n is approximately 1.2. In the present process a typical value of n has been found to be approximately 1, slightly decreasing with decreasing flow rate.

The flow rate may vary from 5 ml/min. to 5 l/min. dependent on the orifice diameter and the desired particle diameter.

It should be born in mind that D50 in the above formula represents the mean particle diameter of the particles as emulsified and since the emulsified particles are subsequently washed and dried some controlled shrinking takes place whereby the final particle diameter is reduced.

BRIEF DESCRIPTION OF THE DRAWINGS

The invention is further described with reference to the drawings, wherein.

DESCRIPTION OF PREFERRED EMBODIMENTS

Figure 1:
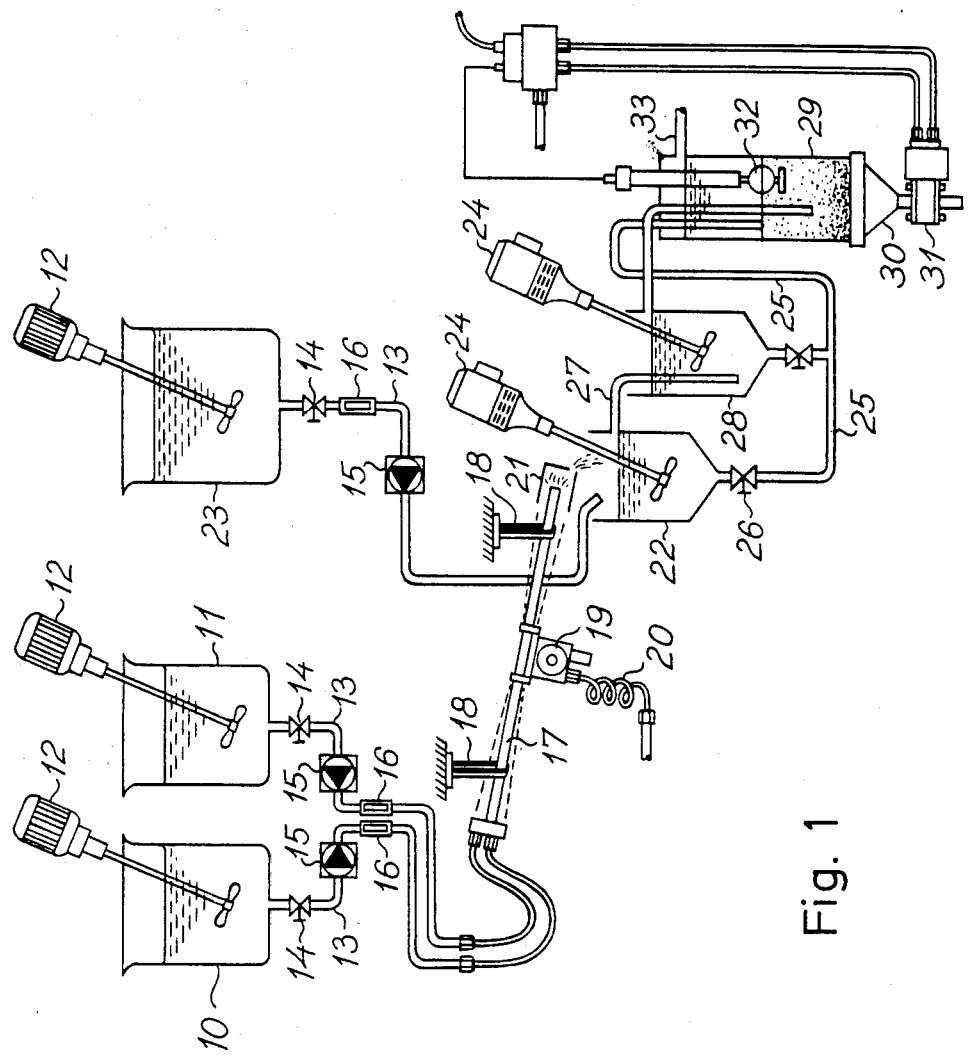
FIG. 1 diagrammatically shows a first embodiment of an apparatus for carrying out the method according to the invention.

A container 10 for a solution of a polymerizable substance and a container 11 for a first liquid are provided with stirrers 12 and outlet conduits 13 which are fitted with manually operatable valves 14, pumps 15 and flow meters 16 for controlling the flow rate of the solution of the polymerizable substance and the first liquid.

The solution and the first liquid are simultaneously and continuously fed into an inlet end of a tube 17 which is elastically suspended at an acute angle to the horizontal plane by means of rubber bands 18 and which is vibrated by means of a ball vibrator 19 operated by means of compressed air supplied from a suitable source through a flexible conduit 20.

The resulting emulsion of the solution of the polymerizable substance and the first liquid flows from an outlet end of the tube 17 around which a hood 21 is arranged to catch and direct the flow of the emulsion into a receptacle 22 which contains a second liquid. The second liquid is fed into the receptacle 22 from a container 23 which is similarly provided with a stirrer 12, outlet conduit 13, valve 14, pump 15 and flow meter 16. The receptacle 22 is equipped with a stirrer 24 and an outlet conduit 25 fitted with a manually operated valve 26. Close to the top of the receptacle 22 another conduit 27 feeds the overflow from the receptacle 22 into a similar, and similarly equipped, receptacle 28. The conduit 25 feeds the contents of the receptacles 22 and 28 into a container 29 for the separation of the phases and sedimentation of the polymerized, substantially spherical particles of the polymerizable substance.

A funnel 30 for drawing off the sedimented polymerized particles is arranged at the bottom of the container 29. The funnel 30 is fitted with a valve 31 operated by means of a level transducer 32 which opens the valve 31 when the level of the second liquid rises and closes the valve 31 when the level of the second liquid sinks to a predetermined level. A conduit 33 for the overflow of the first liquid (which forms a separate phase on top of the second liquid due to its lower density) is provided close to the top of the container 29.

Figure 2:
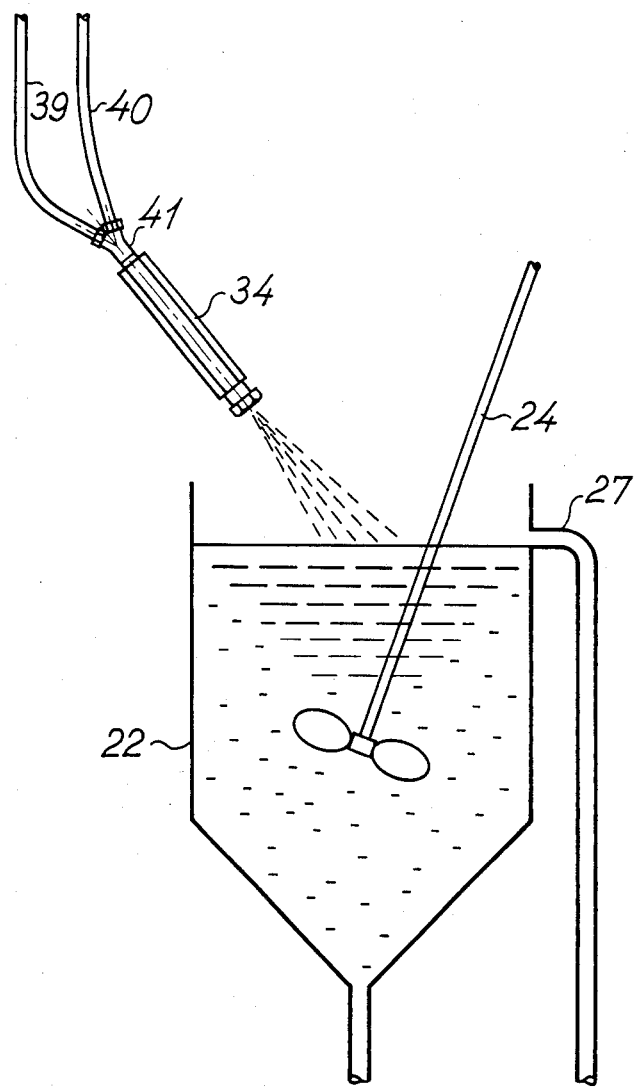
FIG. 2 is a diagrammatic illustration of a second, more preferred apparatus for carrying out the method according to the invention.
Figure 3:
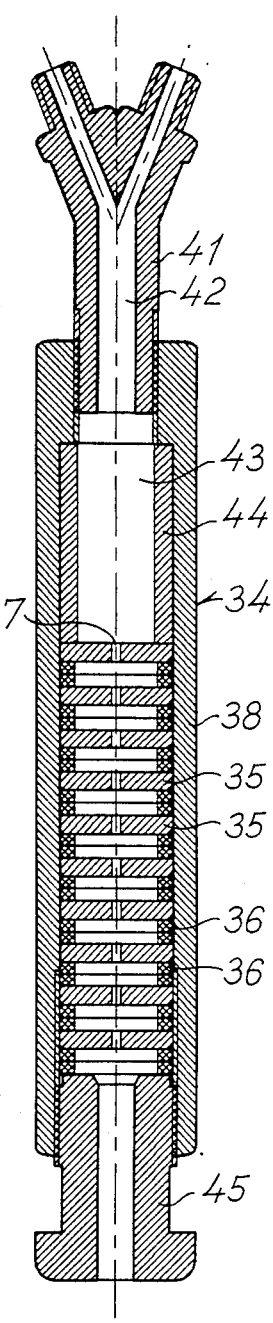
FIG. 3 is a sectional view in an enlarged scale of a nozzle unit of the apparatus shown in FIG. 2.

In the apparatus shown in FIGS. 2 and 3 the emulsion is produced in a nozzle unit 34 having a tubular housing 38 in which a number of axially spaced orifice discs 35 is placed in series. The distance between the discs is determined by annular spacer members 36. Each disc has a central circular bore 37 formed therein with a diameter which is usually the same for all of the discs and which is preferably within the range of 0.5–5 mm.

The other parts of the apparatus shown in FIGS. 2 and 3 are quite similar to those described in FIG. 1. The solution of a polymerizable substance and the first liquid are fed to the nozzle unit through a pair of separate conduits 39 and 40, respectively. These conduits are connected to a fitting 41 in which the flow passages of the conduits are united to a common bore 42, which communicates with an entrance chamber 43 defined within a cylindrical spacer member 44. The emulsion levels the nozzle unit through an outlet nozzle 45 as a jet directed down into the receptacle 22, which contains a second liquid.

The invention is further described in the following examples.

EXAMPLE 1

50 ml of a commercially available aqueous sodium silicate solution (36% w/w; $Na_2O(SiO_2)_{3.3}$) was diluted with 75 ml of water. 0.6 g of glycerol monooleate was added to 120 ml of ISOPAR G (available from Esso), and the mixture was poured into a beaker provided with a stirrer (HomoRex, voltage regulated, optimal stirring at 110–150 V). The aqueous solution of sodium silicate was added and emulsified in the ISOPAR by stirring for 30 seconds.

The emulsion was then poured into 550 ml of an acetate buffer (pH 4.8) with vigorous stirring after which the mixture was left to stand for 15 minutes resulting in a separation of the phases. The gelled particles of silicic acid were partially precipitated in the aqueous phase in which the pH had increased to 5.3.

The ISOPAR phase was decanted off, the aqueous phase was filtered and the filter cake was washed with water and dried at 120° C. for 24 hours.

The resulting particles had a mean diameter D50 (cf. the definition given above) of 21.4 μm, and a slope (cf. the definition given above) of 6.17. The particle diameter was determined from the angle of scatter light, as explained above, in a Microtrack apparatus (manufactured by Leeds and Northrop).

EXAMPLE 2

The sodium silicate solution and the ISOPAR G/glycerol monooleate mixture of Example 1 were simultaneously and continuously fed into a tube with an inner diameter of 18 mm and a length of 1 m at a flow rate of 40 g/min. and 25 g/min., respectively, while vibrating the tube at a frequency of 100 Hz and with an amplitude of 5 mm at the middle of the tube and 2.5 cm and either end of the tube by means of a ball vibrator located at the middle of the tube, substantially as shown in the drawing.

The sodium silicate droplets were gelled, filtered and dried as described in Example 1.

The resulting particles had a mean diameter D50 of 9.95 μm and a slope of 2.46 when determined as described in Example 1.

EXAMPLE 3

By processing substantially as described in Example 2 with the exception that the flow rate through the tube was doubled, silica particles were obtained which had a mean diameter D50 of 11.36 μm and a slope of 2.63 when determined as described in Example 1.

EXAMPLE 4

By proceeding substantially as described in Example 1 with the exception that no emulsifier was added to the ISOPAR, substantially spherical silica particles were obtained which had a mean diameter D50 of 28.36 μm and a slope of 13.46 when determined as described in Example 1. From this figure, it appears that the particle size distribution is larger than is satisfactory when no emulsifier is included in the ISOPAR.

EXAMPLE 5

A suspension in 18% HCl of silica particles prepared substantially as described in Example 2 with the exception that the concentration of sodium silicate was 11.86% were subjected to ageing by heat treatment at various temperatures and for varying periods of time. The particles in sample A were treated at 25° C. for 30 minutes, the particles in sample B were treated at 110° C. for 30 minutes, and the particles in sample C were treated for 4 hours at 110° C. The particles in each sample were then rinsed with deionized water and dried in an oven at 140° C.

The pore diameter and pore volume (measured chromatographically substantially as described in *Journal of Chromatography*, 83 (1973) 111–124, Elsevier Scientific Publishing Company, Amsterdam, CHROM 6803, Krefeld, van, M. E. and Hoed, van den, N. "Mechanism of Gel Permeation Chromatography; Distribution Coefficient") of the particles in each sample are shown in Table 1.

TABLE 1

|   | Pore volume (cm³/g) | Pore diameter (Å) |
|---|---|---|
| A | 0.59 | 53 |
| B | 1.2 | 95 |
| C | 1.6 | 150 |

It appears from the table that it is possible to obtain a desired pore diameter and pore volume by adjusting the temperature and period for the heat treatment.

EXAMPLE 6

Silica particles prepared as described in Example 5 were calcinated at 450° C. for 3 hours to obtain a greater compressive strength of the particles. In this way, the column pressure drop in a chromatographic column is decreased because fewer particles collapse under the pressure used to pack a chromatographic column.

The effect of the calcination appears from Table 2.

TABLE 2

|   | Before calcination | After calcination |
|---|---|---|
| Pore diameter (Å) | 116 | 108.2 |
| Pore volume (cm³/g) | 1.21 | 1.145 |
| Column pressure drop (bars) | 110 | 65 |

EXAMPLE 7

Two series of tests were made with the same raw materials as described in Example 1 but instead of producing the emulsion in a vibrating tube it was made by conducting the silicate solution and the ISOPAR G/glycerol monooleate mixture through a nozzle arrangement as shown in FIGS. 2 and 3. Nine orifice discs were arranged in series.

In a first test series (graph A in FIG. 4) an orifice diameter of 0.8 mm was used. In a second test series (graph B in FIG. 4) the orifice diameter was 0.6 mm.

Figure 4:
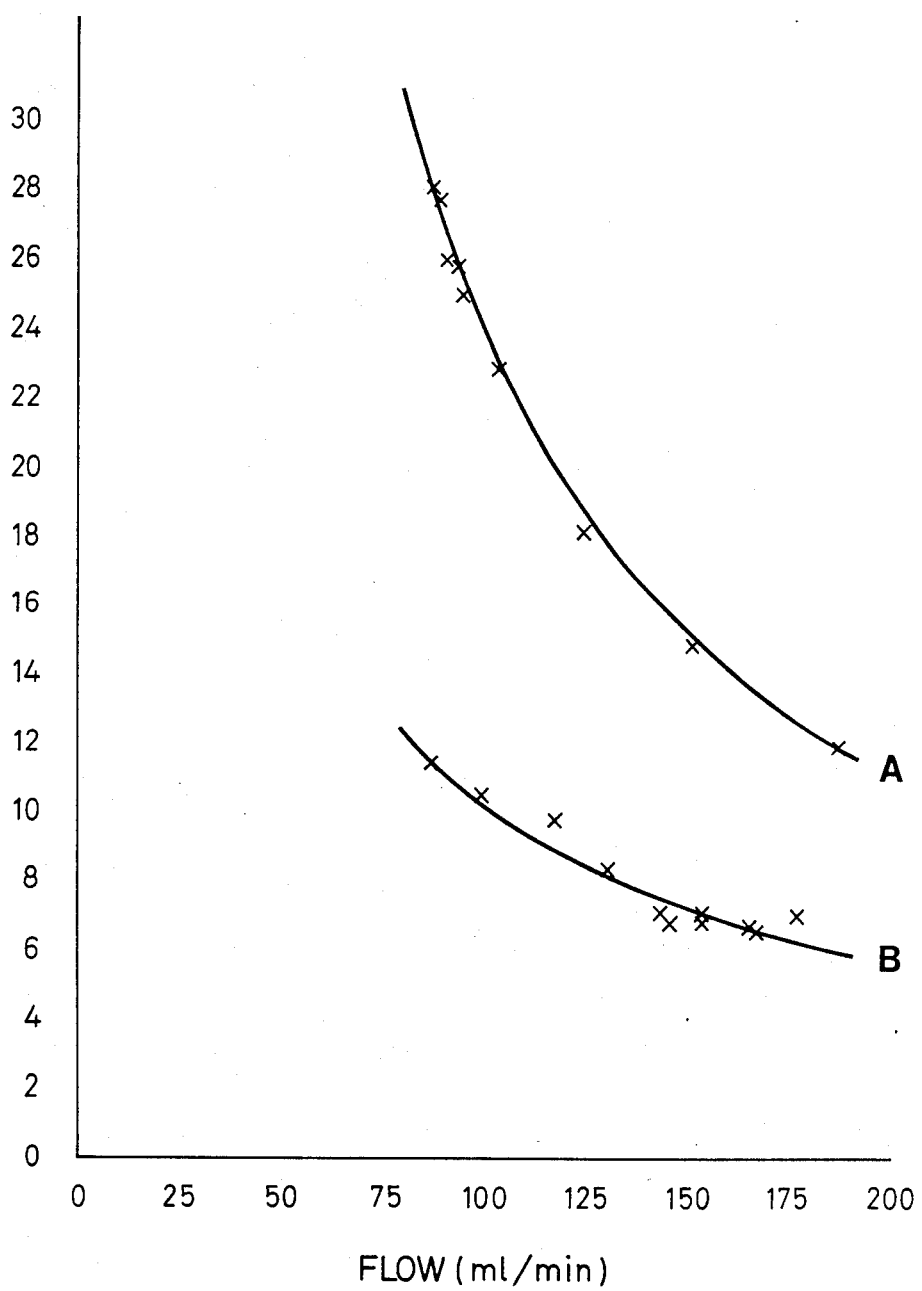
FIG. 4 is a graphic representation in which the mean particle diameter is plotted versus flow rate through the nozzle unit shown in FIG. 3.

The test results are illustrated graphically in FIG. 4 in which the abscissa represents the flow rate in ml/min. and the ordinate D50 in μm.

Approximate relations between D50 and flow rate F are as follows:

For the A series: $D50 \times F^{1.12} = 4152$

For the B series: $D50 \times F^{0.85} = 509$.

I claim:

1. A process for preparing substantially spherical solid particles of a substantially uniform particle size, said method comprising:
    (a) dispersing a solution of a polymerizable substance in a first liquid with which said solution is immiscible by means of a suitable emulsifier to form an emulsion having droplets of the solution of the polymerizable substance of a substantially uniform particle size as the dispersed phase, (b) pouring the emulsion into a second liquid which is miscible with said solution but immiscible with said first liquid and which contains a sufficient amount of a reactant to polymerize the polymerizable substance to form said substantially spherical solid particles, (c) separating a phase containing said first liquid from a phase containing said second liquid and said solid particles, and (d) recovering said solid particles from said second liquid.

2. A process according to claim 1, in which the polymerizable substance is an inorganic gel-forming compound.

3. A process according to claim 1, in which the emulsion is a water-in-oil type emulsion.

4. A process according to claim 2, in which the inorganic gel-forming compound is selected from the group consisting of alkali metal silicates, aluminates and zirconates.

5. A process according to claim 4, in which the alkali metal silicate is sodium silicate.

6. A process according to claim 2, in which the inorganic gel-forming compound is a silica sol.

7. A process according to claim 1, in which the first liquid is an organic liquid the density of which differs significantly from that of the second liquid.

8. A process according to claim 7, in which the organic liquid is a hydrocarbon.

9. A process according to claim 7, in which the organic liquid is a coparaffinate.

10. A process according to claim 1, in which the second liquid is miscible with the liquid in which the polymerizable substance is dissolved.

11. A process according to claim 1, in which the second liquid is water.

12. A process according to claim 1, in which the polymerization reactant is an acid or an acid buffer.

13. A process according to claim 1, in which the average particle size of the polymerized particles is in the range of about 1–100 μm.

14. A process according to claim 13, in which the particle size distribution does not substantially exceed a slope of 7 (as defined in the specification).

15. A process according to claim 1, in which an aqueous solution of an alkali metal silicate such as sodium silicate is dispersed in a coparaffinate by means of the emulsifier, the emulsion formed being poured into an aqueous solution of the polymerization reactant to form gelled, substantially spherical hydrated silica particles.

16. A process according to claim 15, in which the aqueous solution of the alkali metal silicate is an aqueous solution of sodium silicate in a concentration of 8–20%.

17. A process according to claim 15, in which the sodium silicate is sodium silicate of the formula $Na_2O(SiO_2)_x$, wherein x is 3–4.

18. A process according to claim 15, in which the emulsifier is an emulsifier with an HLB value of less than 6.

19. A process according to claim 18, in which the emulsifier is selected from the group consisting of monoesters of $C_{14-20}$ fatty acids.

20. A process according to claim 15, in which the second liquid is an aqueous buffer of a pH in the range of 4–7, which is present in a volume sufficient to maintain a final pH in the mixture of the emulsion and the second liquid of below 7.

21. A process according to claim 20, in which the buffer is an acetate buffer, and the final pH of the mixture is about 5.3.

22. A process according to claim 15, in which the polymerized, substantially spherical hydrated silica particles are subjected to heat treatment in an aqueous medium of a pH of less than 8 and at a temperature above 80° C.

23. A process according to claim 22, in which the heat treatment is performed by boiling in the second liquid.

24. A process according to claim 1, in which the polymerizable substance is dispersed in the first liquid by simultaneously and continuously feeding the solution of the polymerizable substance and the first liquid, which contains the emulsifier, into a substantially cylindrical, elongated passage defined in a body member at such a flow rate that the passage is only partly filled up by the liquids to be emulsified, and by vibrating the body member.

25. A process according to claim 1, in which the solution of the polymerizable substance and the first liquid, which contains the emulsifier, is simultaneously driven through at least one orifice.

26. A process according to claim 25, in which the solution of the polymerizable substance and the first liquid is driven through a plurality of orifices arranged in series.

27. A process according to claim 25, in which the orifice is a circular hole with a diameter of 0.5–5 mm.

28. A process according to claim 27, in which the total liquid volume flow rate through the circular hole is 5 ml/min.–5 l/min.

29. A process according to claim 14, wherein the particle size distribution does not substantially exceed a slope of 3.

30. A process according to claim 18, wherein said emulsifier has an HLB value between 2 and 5.

31. A process according to claim 19, wherein said emulsifier is selected from the group consisting of monoesters of $C_{16-18}$ fatty acids.

32. A process for preparing substantially spherical solid particles of an inorganic gel having a substantially uniform particle size, said method comprising:

(a) dispersing an aqueous solution of an inorganic gel-forming compound in a first liquid with which said solution is immiscible by means of a suitable emulsifier to form an emulsion having droplets of the solution of the inorganic gel forming compound of a substantially uniform particle size as the dispersed phase;

(b) pouring said emulsion into a second liquid which is miscible with said solution but immiscible with said first liquid and which contains a sufficient amount of a reactant to form said substantially spherical solid inorganic gel particles from said gel forming compound, (c) separating a phase containing said first liquid from a phase containing said second liquid and said inorganic gel particles, and (d) recovering said inorganic gel particles from said phase containing said second liquid.

33. A process according to claim 32, wherein said inorganic gel forming compound is selected from the group consisting of alkali metal silicates, aluminates and zirconates.

34. A process according to claim 33, wherein said inorganic gel forming compound is sodium silicate.

35. A process according to claim 32, wherein said reactant is a buffer having a pH in the range of 4 to 7.

* * * * *